US00PP32518P2

(12) United States Plant Patent
Vlielander

(10) Patent No.: US PP32,518 P2
(45) Date of Patent: Nov. 24, 2020

(54) ***KALANCHOE* PLANT NAMED 'DOKALWELCH'**

(50) Latin Name: *Kalanchoe blossfeldiana*
Varietal Denomination: Dokalwelch

(71) Applicant: DUMMEN GROUP B.V., De Lier (NL)

(72) Inventor: Ike Vlielander, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,997

(22) Filed: Jan. 13, 2020

(30) Foreign Application Priority Data

Nov. 14, 2019 (QZ) ..... PBR 2019/2995

(51) Int. Cl.
*A01H 5/02* (2018.01)
*A01H 6/32* (2018.01)

(52) U.S. Cl.
USPC ..... Plt./340

(58) Field of Classification Search
USPC ..... Plt./263.1, 355, 340
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Kalanchoe* plant named 'Dokalwelch', characterized by its relatively compact, upright and uniformly mounded plant habit; moderately vigorous growth habit; freely branching plant habit; glossy dark green-colored leaves; uniform and freely flowering habit; double bright orange-colored flowers; and excellent postproduction longevity.

1 Drawing Sheet

Botanical designation: *Kalanchoe blossfeldiana.*
Cultivar denomination: 'DOKALWELCH'.

BACKGROUND OF THE INVENTION

The present invention relates to a new and distinct *Kalanchoe* plant, botanically known as *Kalanchoe blossfeldiana* and hereinafter referred to by the name 'Dokalwelch'.

The new *Kalanchoe* is a product of a planned breeding program conducted by the Inventor in De Lier, The Netherlands. The objective of the breeding program is to create new freely-branching and freely-flowering *Kalanchoe* plants with double-type flowers and attractive leaf and flower coloration.

The new *Kalanchoe* plant originated from a cross-pollination made by the Inventor in De Lier, The Netherlands in August, 2008 of *Kalanchoe blossfeldiana* 'Sanga', not patented, as the female, or seed, parent with *Kalanchoe blossfeldiana* 'Ficalanjamaica', disclosed in U.S. Plant Pat. No. 22,852, as the male, or pollen, parent. The new *Kalanchoe* plant was discovered and selected by the Inventor as a single flowering plant from within the progeny of the stated cross-pollination in a controlled environment in De Lier, The Netherlands in August, 2010.

Asexual reproduction of the new *Kalanchoe* plant by vegetative terminal cuttings in a controlled environment in De Lier, The Netherlands since 2011 has shown that the unique features of this new *Kalanchoe* plant are stable and reproduced true to type in successive generations.

SUMMARY OF THE INVENTION

Plants of the new *Kalanchoe* have not been observed under all possible combinations of environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Dokalwelch'. These characteristics in combination distinguish 'Dokalwelch' as a new and distinct *Kalanchoe* plant:

1. Relatively compact, upright and uniformly mounded plant habit.
2. Moderately vigorous growth habit.
3. Freely branching plant habit.
4. Glossy dark green-colored leaves.
5. Uniform and freely flowering habit.
6. Double bright orange-colored flowers.
7. Excellent postproduction longevity.

Plants of the new *Kalanchoe* can be compared to plants of the female parent, 'Sanga'. Plants of the new *Kalanchoe* differ from plants of 'Sanga' in the following characteristics:

1. Plants of the new *Kalanchoe* are larger than plants of 'Sanga'.
2. Plants of the new *Kalanchoe* flower later than plants of 'Sanga'.
3. Plants of the new *Kalanchoe* have double-type flowers whereas plants of 'Sanga' have single-type flowers.
4. Plants of the new *Kalanchoe* and 'Sanga' differ in flower color as plants of 'Sanga' have darker orange-colored flowers than plants of the new *Kalanchoe.*

Plants of the new *Kalanchoe* can be compared to plants of the male parent, 'Ficalanjamaica'. Plants of the new *Kalanchoe* differ from plants of 'Ficalanjamaica' in the following characteristics:

1. Leaves of plants of the new *Kalanchoe* are smaller than leaves of plants of 'Ficalanjamaica'.
2. Plants of the new *Kalanchoe* flower earlier than plants of 'Ficalanjamaica'.

3. Plants of the new *Kalanchoe* and 'Ficalanjamaica' differ in flower color as plants of the new *Kalanchoe* have bright orange-colored flowers whereas plants of 'Ficalanjamaica' have bright yellow-colored flowers.

Plants of the new *Kalanchoe* can be compared to plants of the *Kalanchoe blossfeldiana* 'Ficalanhawn', disclosed in U.S. Plant Pat. No. 23,446. In side-by-side comparisons, plants of the new *Kalanchoe* differ primarily from plants of 'Ficalanhawn' in the following characteristics:

1. Plants of the new *Kalanchoe* are more compact than plants of 'Ficalanhawn'.
2. Leaves of plants of the new *Kalanchoe* are smaller than leaves of plants of 'Ficalanhawn'.
3. Plants of the new *Kalanchoe* have slightly smaller flowers than plants of 'Ficalanhawn'.
4. Plants of the new *Kalanchoe* and 'Ficalanhawn' differ in flower color as plants of 'Ficalanhawn' have darker orange-colored flowers than plants of the new *Kalanchoe*.

BRIEF DESCRIPTION OF THE PHOTOGRAPH

The accompanying colored photograph illustrates the overall appearance of the new *Kalanchoe* plant showing the colors as true as it is reasonably possible to obtain in colored reproductions of this type. Colors in the photograph may differ slightly from the color values cited in the detailed botanical description which accurately describe the colors of the new *Kalanchoe* plant.

The photograph (FIG. 1) is a side perspective view of a typical flowering plant of 'Dokalwelch' grown in a container.

DETAILED BOTANICAL DESCRIPTION

The aforementioned photograph and following observations, measurements and values describe plants grown during the autumn in 10-cm containers in a glass-covered greenhouse in De Lier, The Netherlands and under cultural practices typical of commercial *Kalanchoe* production. During the production of the plants, day temperatures ranged from 18° C. to 20° C., night temperatures averaged 18° C. and light levels ranged from 10,000 lux to 50,000 lux. Plants received long day/short night conditions (more than 14 hours of light) for three weeks then plants received photoinductive short day/long night conditions (minimum 14 hours darkness) until flowering. Plants were 16 weeks old when the photograph and the description were taken. In the detailed description, color references are made to The Royal Horticultural Society Colour Chart, 2007 Edition, except where general terms of ordinary dictionary significance are used.

Botanical classification: *Kalanchoe blossfeldiana* 'Dokalwelch'.

Parentage:

*Female, or seed, parent.*—*Kalanchoe blossfeldiana* 'Sanga', not patented.

*Male or pollen parent.*—*Kalanchoe blossfeldiana* 'Ficalanjamaica', disclosed in U.S. Plant Pat. No. 22,852.

Propagation:

*Type.*—By vegetative terminal cuttings.

*Time to initiate roots, summer.*—About 12 days at temperatures about 21° C.

*Time to initiate roots, winter.*—About 16 days at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Fine, fibrous; typically greyish white to reddish brown in color, actual color of the roots is dependent on substrate composition, water quality, fertilizer type and formulation, substrate temperature and physiological age of roots.

*Rooting habit.*—Moderately freely branching; medium density to sparse.

Plant description:

*Plant and growth habit.*—Relatively compact, upright and uniformly mounded plant habit; freely flowering habit with numerous cymes positioned above the foliar plane; triangular in shape with rounded crown; appropriate for 10 to 15-cm containers; moderately vigorous growth habit; moderate growth rate.

*Plant height at flowering.*—About 15 cm.

*Plant diameter at flowering.*—About 16 cm.

*Branching habit.*—Freely branching habit with about five to seven lateral branches developing per plant; pinching (removal of the terminal apex) is not required but will enhance lateral branch development.

Lateral branch description:

*Length.*—About 8 cm to 10 cm.

*Diameter.*—About 2 mm to 4 mm.

*Internode length.*—About 1 cm to 2 cm.

*Aspect.*—Mostly upright.

*Strength.*—Moderately strong.

*Texture and luster.*—Smooth, glabrous; semi-glossy.

*Color, developing and developed.*—Close to 137B.

Leaf description:

*Arrangement.*—Opposite, simple; generally symmetrical.

*Length.*—About 10 cm.

*Width.*—About 6.5 cm.

*Shape.*—Ovate to elliptic.

*Apex.*—Obtuse.

*Base.*—Obtuse.

*Margin.*—Vaulted.

*Texture and luster, upper surface.*—Smooth, glabrous; coriaceous; succulent; glossy.

*Texture and luster, lower surface.*—Smooth, glabrous; coriaceous; succulent; matte.

*Venation pattern.*—Pinnate.

*Color.*—Developing and fully developed leaves, upper surface: Close to 147A; venation, close to 147A. Developing and fully developed leaves, lower surface: Close to 137B; venation, close to 137B.

*Petioles.*—Length: About 7 mm. Diameter: About 4 mm to 8 mm. Strength: Moderately strong. Texture and luster, upper and lower surfaces: Smooth, glabrous; coriaceous; succulent; glossy. Color, upper surface: Close to 147A to 147B. Color, lower surface: Close to 137B.

Flower description:

*Flower arrangement and habit.*—Double-type flowers arranged in axillary cymes; uniform and freely flowering habit with usually more than 25 open flowers and more than 25 flower buds per lateral branch and more than 150 open flowers and flower buds developing per plant; plants flower continuously for at least seven weeks; flowers face mostly upright to outwardly depending on the position in the inflorescence.

*Fragrance*.—None detected.

*Natural flowering season*.—Plants of the new *Kalanchoe* initiate and develop flowers under short day/long night conditions or during November and December in the Northern Hemisphere; flower initiation and development can also be induced under artificial short day/long conditions (at least 14 hours of darkness).

*Time to flower*.—Uniform flowering habit, under short day/long night photoinductive conditions, plants begin flowering about 11 to 13 weeks; actual time to flower is primarily dependent upon temperature and light intensity.

*Post-production longevity*.—Excellent post-production longevity; plants maintain good foliage and flower substance for about 43 days under interior conditions; individual flowers last about 17 days on the plant; flowers persistent.

*Flower diameter*.—About 1.5 cm.

*Flower length* (*height*).—About 1.7 cm.

*Flower buds*.—Length: About 9 mm. Diameter: About 4 mm. Shape: Ovoid. Texture and luster: Smooth, glabrous; glossy. Color: Close to 138A.

*Petals and petaloids*.—Arrangement: About 18 to 22 petals in multiple whorls. Length: About 6 mm to 8 mm. Width: About 4 mm to 5 mm. Aspect: Flat to slightly upright. Shape: Ovate. Apex: Acute. Base: Obtuse. Margin: Entire. Texture and luster, upper and lower surfaces: Smooth, glabrous; slightly glossy. Color: When opening, upper surface: Close to 28A. When opening, lower surface: Close to between 24D and 25D. Fully opened, upper surface: Close to 28B; venation, close to 28B; color becoming closer to 28A to 28B with development. Fully opened, lower surface: Close to between 24D and 25D; venation, close to between 24D and 25D; color does not change with development.

*Sepals*.—Appearance: Four in a single whorl. Length: About 7 mm. Width: About 2 mm. Shape: Oblong, pointed. Apex: Acute. Base: Obtuse. Margin: Entire. Aspect: Upright, rigid. Texture and luster, upper and lower surfaces: Smooth; glabrous; slightly glossy. Color, upper and lower surfaces: Close to 138A.

*Peduncles*.—Length: About 2 mm to 5 mm. Diameter: About 1 mm to 2 mm. Aspect: Erect, rigid. Strength: Strong. Texture: Smooth, glabrous. Color: Close to 138A.

*Reproductive organs*.—Androecium: Stamen number: If present, about eight per flower. Filament length: About 3 mm. Filament color: Close to 155C. Anther size: About 0.1 mm by 0.3 mm. Anther shape: Elliptic, flat. Anther color: Close to 150D. Amount of pollen: Scarce. Pollen color: Close to 12A. Gynoecium: Pistil number: About four to eight. Pistil length: About 8 mm. Style length: About 7 mm. Style color: Close to 138D. Stigma shape: Flat. Stigma color: Close to 8D, crystalline. Ovary color: Close to 138D.

*Seeds*.—Quantity per flower: If developed, up to 30 seeds per flower. Length: About 0.1 mm. Diameter: About 0.05 mm. Texture: Rough. Color: Close to 166C.

Temperature tolerance: Plants of the new *Kalanchoe* have been observed to tolerate temperatures from about 16° C. to about 35° C.

Pathogen & pest resistance: To date, plants of the new *Kalanchoe* have not been observed to be resistant to pathogens and pests common to *Kalanchoe* plants.

It is claimed:

1. A new and distinct *Kalanchoe* plant named 'Dokalwelch' as illustrated and described.

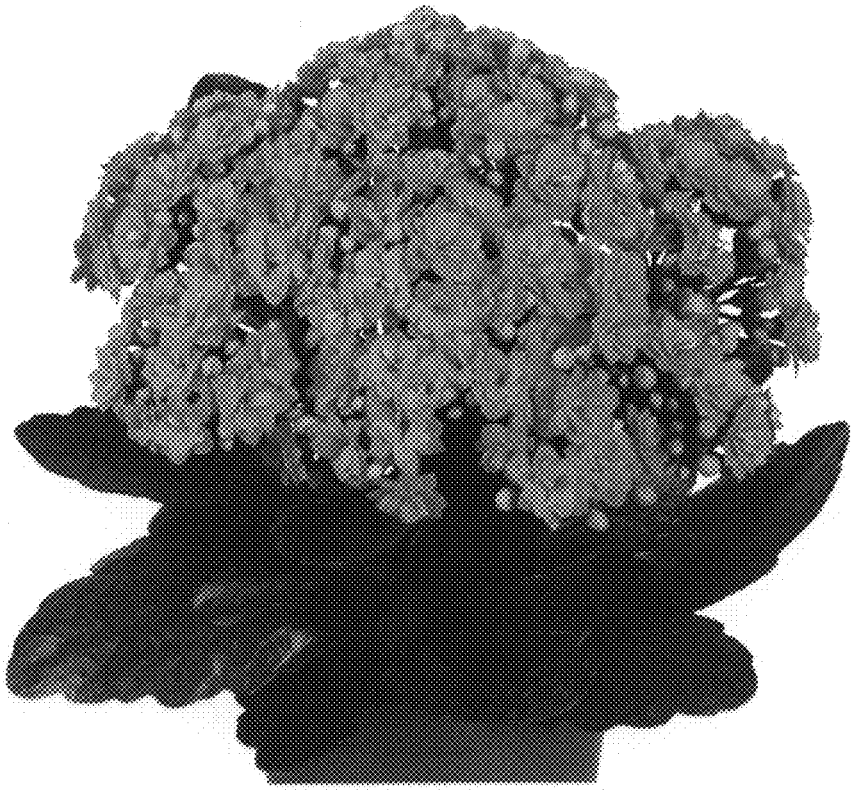

* * * * *